United States Patent [19]

Ehara et al.

[11] Patent Number: 4,770,027

[45] Date of Patent: Sep. 13, 1988

[54] METHOD OF MEASURING CONCENTRATIONS OF ODORS AND A DEVICE THEREFOR

[76] Inventors: Katuo Ehara, 4-18-6, Kamisaginomiya, Nakano-ku, Tokyo; Takeo Koizumi, 127-14, Nishiterao-machi, Kanagawa-ku, Yokohama; Yasusuke Wakabayashi, 28-1, Chuo-machi, Kurume-shi, Fukuoka-ken, all of Japan

[21] Appl. No.: 935,491

[22] Filed: Nov. 26, 1986

[30] Foreign Application Priority Data

Mar. 24, 1986 [JP] Japan .................................. 61-66468
Mar. 26, 1986 [JP] Japan .................................. 61-45347
Jun. 5, 1986 [JP] Japan .................................. 61-131214
Jun. 19, 1986 [JP] Japan .................................. 61-144317

[51] Int. Cl.⁴ .......................................... G01N 31/00
[52] U.S. Cl. .......................................... 73/23; 422/83
[58] Field of Search ............... 73/23, 27 R; 422/88, 422/90, 98, 83; 340/632, 634; 357/25; 204/1 T

[56] References Cited

U.S. PATENT DOCUMENTS

| | | | |
|---|---|---|---|
| 3,028,490 | 4/1962 | Guilleux | 340/632 |
| 3,635,282 | 1/1972 | Watanabe | 340/634 |
| 4,145,913 | 3/1979 | Brown et al. | 73/23 |
| 4,397,888 | 8/1983 | Yannopoulos et al. | 340/634 |
| 4,399,687 | 8/1983 | Collins | 73/23 |
| 4,505,146 | 3/1985 | Miners | 73/23 |
| 4,563,893 | 1/1986 | Tanyolac et al. | 73/23 |
| 4,644,333 | 2/1987 | Barendsz et al. | 73/23 |

Primary Examiner—Stewart J. Levy
Assistant Examiner—Hezron E. Williams
Attorney, Agent, or Firm—Jones, Tullar & Cooper

[57] ABSTRACT

The invention involves the measurement of the total concentration of odors of an article such as foodstuff, fruits and beverages as an indication of their specific quality such as freshness and maturity. An odorimetric device includes a non-selective odor detector disposed within an odorimetric chamber and a heater means for heating the odor detector to a predetermined operating temperature. The odor detector is comprised of a sintered body or film of a highly purified n-type metal oxide semiconductor formed on a substrate by vapor deposition. In one embodiment, the total concentration of odors of an object that is monitored as a function of time may be compared with a reference value or pattern to evaluate the quality of the object. In a second embodiment, the odor detector is comprised of a plurality of like odor detector elements with their sensing characteristics staggered due to different operating temperatures set by their associated heater elements, each odor detector element generating a signal indicative of the total concentration of the odors. The use of this composite odor detector enables a more reliable determination of the quality of an object in reference to a reference object.

23 Claims, 3 Drawing Sheets

METHOD OF MEASURING CONCENTRATIONS OF ODORS AND A DEVICE THEREFOR

BACKGROUND OF THE INVENTION

1. Field of the Invention

The present invention relates to the field of odorimetry and, more particularly, to a method of measuring the total concentration of odors of an object, a method of discriminating objects by comparatively analyzing the concentrations of various odors of the objects, and an apparatus for use in carrying out such methods.

2. Description of the Prior Art

Odorimetry plays an important role in the field of quality inspection, for example, when the freshness of perishable foods being shipped is to be evaluated. Other examples include control of fermentation and classification by grade of seaweed, coffee, alcoholic beverages or the like in accordance with odor concentrations. For such quality inspections, it is required not so much to measure individual odors separately but to monitor the total concentration of the odors instantaneously.

Conventionally, the above-mentioned quality inspections have been carried out by odor organoleptic tests, i.e., by the human sense of smell. However, such inspections are possible by only those who have a keen sense of smell and taste as well and also are well trained to perform such inspections. Such training takes a long time. Further, the results of the inspections may differ depending upon the physical conditions of the inspector.

Thus, because of lack of objectivity, it has been recognized that it is difficult to provide an acceptable method of odor measurement which can be used to automatically monitor quality inspection processes.

In the fields of cosmetics or liquors, on the other hand, odors play an important role in determining their quality, thus necessitating quality inspection through analytical measurement of odors. Gas chromatography has frequently been used in the art for the purpose of measuring individual odors separately. The gas chromatography, however, is defective in the following points: (1) The results of measurement vary depending upon particular sampling method used; (2) The measurement has to be carried out by a person skilled to some extent; (3) The apparatus useful for such measurement is relatively costly; and (4) It take a considerable time before the results of measurement are given. Taking the last point (4) into consideration, it can be said that gas chromatography is not suited for an in-situ measurement where it is necessary to provide a real time indication of the concentration of odors.

SUMMARY OF THE INVENTION

It is, therefore, a principal object of the present invention to provide a method of measuring the total concentration of odors emitting from an object to provide an instanteneous indication thereof.

Another object of the present invention is to provide a method of discriminating objects without resort to the human sense by measuring and analyzing objectively various odors of the objects.

A further object of the present invention is to provide an apparatus useful for carrying out the above-mentioned methods that includes one or more non-selective odor detectors.

According to a first feature of the present invention, there is provided a method of measuring the total concentration of odors of an object using an odorimetric device including a non-selective odor detector disposed within an odorimetric chamber, comprising the steps of: (a) heating a non-selective odor detector to a predetermined temperature at which the rate of adsorption and desorption of odors of an object to be measured is sufficiently high to enable a real time measurement of the total concentration of the odors; (b) introducing fresh air into an odorimetric chamber defined in the odorimetric device to scavenge the odorimetric chamber; (c) placing the object in the odorimetric chamber; (d) sealing off the odorimetric chamber from the surrounding environment; and (e) monitoring the total concentration of the odors of the object through the output reading of the odor detector.

According to a second feature of the present invention, there is provided an odoriometric device for measuring the total concentration of odors of an object, comprising: (a) a housing defining therein an odorimetric chamber for accommodating an object to be measured; (b) a door for sealingly closing the odorimetric chamber from the surrounding environment; (c) an non-selective odor detector mounted within the odorimetric chamber for monitoring the total concentration of odors emitting from the object; (d) heater means for heating the non-selective odor detector to a predetermined temperature at which the rate of adsorption and desorption of odors of the object to be measured is sufficiently high to enable a real time measurement of the total concentration of the odors; (e) means for introducing fresh air into the odorimetric chamber to scavenge it; (f) display means for providing an instantaneous indication of the monitored total concentration of the odors.

BRIEF DESCRIPTION OF THE DRAWINGS

Other objects, features and advantages of the present invention will become apparent from the following description taken in conjunction with the accompanying drawings, in which.

DESCRIPTION OF THE PREFERRED EMBODIMENTS

Figure 1A:
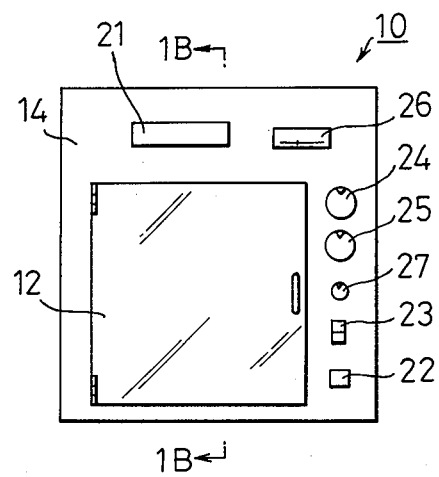
FIG. 1A is a front elevation showing an odorimetric device embodying the present invention.

In the present invention, a non-selective odor detector is used for measuring the total concentration of odors to provide a representative electric signal. The odor detector may be comprised of a plurality of known gas sensors having selective characteristics or of a single non-selective odor detector to be described later in detail. The odor detector used should be capable of detecting the total concentration of odors of a sample, but is not necessarily required to provide a separate indication of the concentration of each order.

When it is desired to provide such separate indication, a plurality of existing selective gas sensors, or alternatively, a plurality of non-selective sensors having their characteristics adjusted in the manner to be described below can be used. Since the selective detectors are well known in the art, the following description is desired exclusively to embodiments incorporating non-selective gas sensors.

The three major requirements for gas detectors utilizing a semiconductor (usually an oxide semiconductor of n-type) which exhibits an electric resistance varying (or decreasing) in response to exposure to gases when it is held at a high temperature are as follows: (1) The detector must have selectivity, i.e., a high sensitivity to gases of interest; (2) It is insensitive to other gases; and (3) The characteristics of the detector must be stable throughout its useful life.

In short, various attempts have been made in the prior art to provide a gas detector which is responsive only to specific gases (or harmful gases) but which does not respond to other kinds detectors to measure odor concentrations will not provide an instantaneous indication of the total concentration of odors, as the detectors are sensitive to only certain specific kinds of gases.

We have painstakingly developed an odor detector for measuring the total concentration of various odors from an object to provide an instantaneous indication thereof, based on the observation that an n-type semiconductor becomes sensitive to a variety of gases containing odors if the purity is raised above a certain level without adding catalysts. One example of such non-selective odor detector comprises a sensor portion formed of a simple substance of an n-type semiconductor, such as tin oxide ($SnO_2$) or zinc oxide ($ZnO$), having its electric resistance varying in response to adsorption and desorption of gas molecules; and a heater for heating the sensor portion to a predetermined operating temperature.

The n-type semiconductor to be used in the sensor portion is of a sintered body or film of the metal oxide. A p-type semiconductor generally is not satisfactorily sensitive to odors. Among various n-type semiconductor materials, the tin oxide and zinc oxide as described above show excellent sensitivity. The sensor portion can be fabricated by conventional techniques such as vacuum deposition, sputtering, chemical treatment (i.e., sintering to provide porosity) or photoetching. In the sintering method, for example, the heat treatment is performed at 600° to 850° C.

It has also been discovered that it is possible to vary the characteristics of such an odor detector by changing the operating temperature through selective adjustment of the heater. It will then be appreciated that a variety of odors diffusing from an object can be detected by a plurality of like detectors which are heated to different predetermined temperatures by their associated heaters.

In a preferred embodiment of the present invention, a voltage of 2 to 6 V is applied to a heater having a resistance of about 10 K$\Omega$. This range of the voltage is selected so as to facilitate the measurement of odors of an object. The present invention should not be limited to that particular voltage range and the resistance value.

It should be noted that in order to increase the adsorption and desorption rates, the odor detector has to be heated preparatory to measurement until it reaches a predetermined temperature (e.g., about 200° C.). The measurement can be started when the electric current flowing through the odor detector has become stable, usually several tens of minutes after the power is switched on.

The odor detector provides an electric signal representative of the total concentration of odors present in a monitored environment. The electric signal is fed to a display which may be a digital or analog display. The electric signal may be supplied to a recorder which can plot odor concentration changing with time.

It should be appreciated that in accordance with another embodiment of the present invention, it is possible to determine the total concentration of odors from an object relative to a reference value. The reference value can be set in a common display and/or recorder useful for measuring the total concentration of the odors. Alternatively, a separate odor detector may be provided just for setting the reference value representative of the concentration of a sample In the latter case, it is convenient to place the measuring detector and the reference detector side by side so that the readings of an object under measurement and of a reference sample may be visually compared with each other. As a further alternative, it is possible to incorporate into a detector an annunciator device which can provide a sound or light signal when the measured concentration is below or above the reference value.

Where it is desired to identify a certain object by means of a plurality of odor detectors, the outputs of the respective detectors are transformed into either corresponding patterns of numerical values or graphical representations which are then compared with stored data to match a particular pattern representative of a known object. If a matching pattern is established, this means that the object being evaluated for its odors is identical to the known object.

Incidentally, it should be understood that the odor detector according to the present invention can not only make a measurement of odor concentration under saturated conditions of a monitored environment but also determines the rate at which odors diffuse in the environment.

The odor detector can be designed so that the sample holder incorporates therein a band heater, the output of the odor detector being fed to the Y-axis input of an X-Y recorder and the temperature representative signal derived from the band heater being applied to the X-axis input. With this arrangement, the rate of volatilation of various odors can be recorded as a function of sensor temperature.

The semiconductor sensor is heated to 350° to 450° C. where it is desired to meausre combustible gases with the present odor detector. Since, however, gases containing odors generally have lower concentrations than such combustible gases, the sensor should be held at a lower temperature (e.g., 200° C.) to enable an efficient and accurate determination of odor concentration.

The present invention will be described in more detail with reference to the accompanying drawings.

Figure 1B:
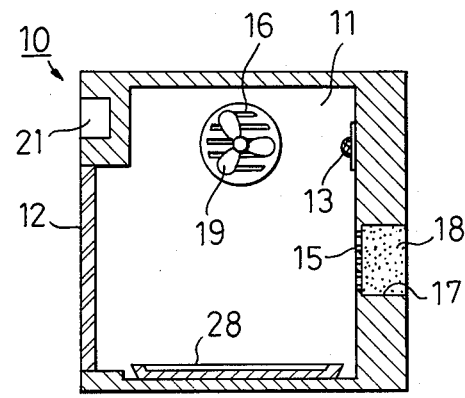
FIG. 1B is a section taken along line 1B—1B of FIG. 1A.

As shown in FIGS. 1A and 1B, an odorimetric device, as generally denoted at reference numeral 10, is constructed of: a housing defining therein an odorimetric chamber 11 for accommodating an object to be measured (not shown); a door 12 for sealingly closing the chamber 11 from the surrounding environment; a non-selective odor detector 13 mounted within the odorimetric chamber 11 for monitoring the total concentration of odors emitting from the object; and a control panel 14, as will be described in the following. All of the inner walls of the odorimetric chamber 11 are lined with stainless steel plates. The houding is formed in its rear wall with air inlet ports 15 and also in its side wall with a gas outlet 16. The rear wall of the housing is formed with an externally opening recess 17 which communicate with the odorimetric chamber 11 through the air inlet ports 15 and in which there are removably charged a filter 18 comprised of surface active sorbent such as activated charcoal. A ventilating fan 19 is provided in the gas outlet 16 for removing the residual odors in the odorimetric chamber. In order to provide for accuracy of measurement, the air inlet ports 15 and the gas outlet 16 may preferably be fitted with doors for shutting off the ambient air from the odorimetric chamber.

The control panel 14 includes: a digital display 21 for providing a digital indication of the total concentration of odors being monitored by the odor detector 13; a main switch 22; a fan switch 23; a voltage regulating knob 24 for regulating the voltage to be applied to the odor detector 13; a fine adjustment knob 25 for finely adjusting the voltage regulated by the knob 24; a voltmeter 26 for indicating the voltage applied to the odor detector 13; and a peak-hold knob 27 for holding the peak of the total concentration of the measured odors. Reference numeral 28 denotes a sample holder for holding thereon a sample or an object to be measured.

Figure 2:
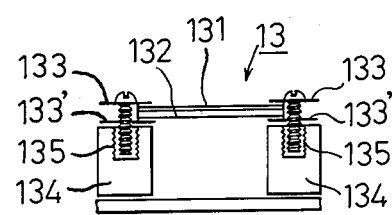
FIG. 2 is a schematic front elevation showing a typical non-selective odor detector incorporated in the odorimetric device of FIGS. 1A and 1B.

Turning to FIG. 2, the non-selective odor detector 13 comprises: a sensor portion 131 formed of a film which is fabricated by coating a substrate or ceramic plate 132 having a thickness of 0.6 mm with a metal oxide (which contains tin oxide having a purity of 99.999% and a binder of aluminum oxide $Al_2O_3$) by vacuum deposition. The sensor portion 131 has its opposite ends sandwiched by a pair of electrodes 133 and 133' therebetween. the electrodes 133 and 133' are placed on a pair of insulators 134. A pair of screws 135 are used to fixedly mount the sensor portion 131 with the electrodes 133 and 133' to the insulators 134.

The odor detector 13 is held at a constant temperature throughout measurement cycles so that it may not be influenced by the ambient temperature and humidity. The odor detector 13 per se has no odor discriminating function but can detect differential concentrations of odors among individual samples of like object which have been treated under different conditions.

In operation, the odor detector 13 is heated to a predetermined operating temperature, which usually takes several tens of minutes after the main switch 22 is turned on. the measurement will commence after the electric current flowing through the odor detector 13 has become stable. The fan switch 23 is turned on to actuate the ventilating fan 19. As a result, the ambient air is filtered through the activated charcoal filter 18 and passes into the odorimetric chamber 11 to deodorize it.

A sample to be used as a reference is placed on the sample holder 28 within the odorimetric chamber 11. Then, the door 12 is closed to shut off the reference sample from the environment outside of the odorimetric chamber 11. With gases containing odors of the sample coming into contact with the odor detector 13, the detector exhibits a change in its electric resistance, causing a corresponding change in the electric current flowing therethrough. This change in the current is derived as a voltage signal, which signal is amplified for display on the digital display 21. This voltage signal may be recorded by a printer (not shown).

Next, the door 12 is opened to remove the reference sample from the odorimetric chamber 11 and then closed. The fan switch 23 is turned on to run the ventilating fan 19. This will introduce fresh air into the odorimetric chamber 11 to ensure that the chamber 11 returns to an odorless state. Then, an object to be measured is placed in the odorimetric chamber 11 to measure the total concentration of odors associated with the object. Thus, the total concentration of the odors of the object can be compared with that of the reference sample.

Figure 3:
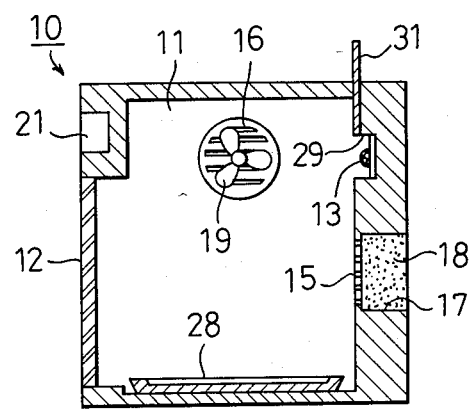
FIG. 3 is a view similar to FIG. 1B but showing an odorimetric device according to a second embodiment of the present invention.

Turning to FIG. 3 showing a second embodiment of the invention, the odorimetric chamber 11 has a recess 29 formed in its rear wall to receive therein the odor detector 13. The recess 29 includes a shutter mechanism 31 operative to isolate the odor detector 13 from the odorimetric chamber 11. This shutter mechanism 31 is of a manually operated type, but may be of an electrically operated type. In this embodiment, a sample is placed into the odorimetric chamber 11 after the chamber 11 is cleaned or qurified with air introduced from the surrounding environment. It is when the plenum of the odorimetric chamber 11 is filled with odors from the sample that the shutter mechanism 31 is actuated to open the recess to the chamber 11 to thereby enable a measurement of the total concentration of the odors without being affected by any other odors. The use of the shutter mechanism 31 also serves to protect the odor detector 13 for its prolonged service life. Like parts or components as used in the embodiment of FIG. 1B are denoted by the same reference numerals in FIG. 3.

The present invention will be described in more detail in connection with the following examples 1 to 5.

EXAMPLE 1

Five non-selective odor detectors of the same type as used in the embodiment of FIG. 2 were assembled into a single composite odor detector. Each of these five odor detectors includes a heater having a resistance of 10 KΩ. The heater associated with the first detector was supplied with a voltage of 2.0 V; the heter for the second detector a voltage of 2.5 V; the third a voltage of 3.0 V; the fourth a voltage of 3.5 V; and the fifth a voltage of 4.0 V, thus resulting in the five detectors having different sensing characteristics.

Figure 4:
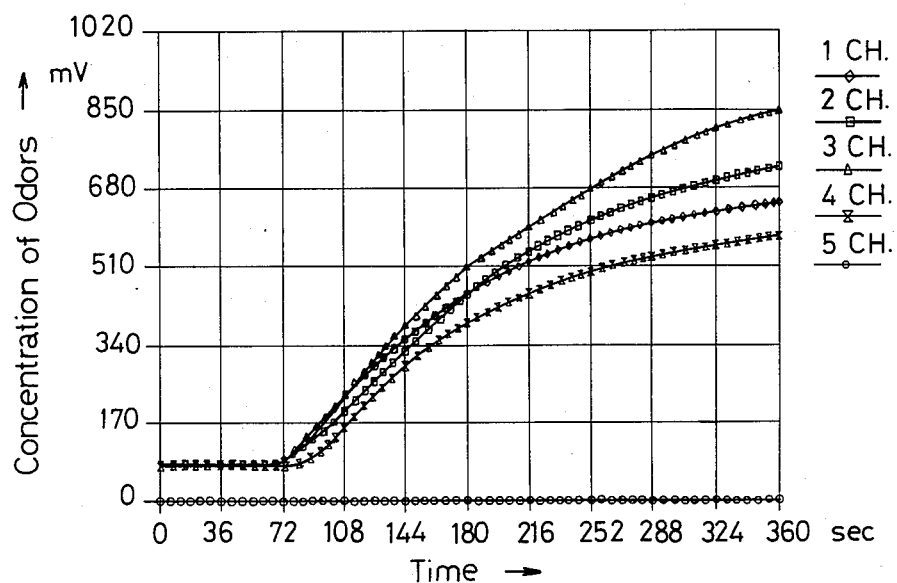
FIG. 4 is a plot against time of the outputs of a plurality of odor detectors, each representative of the total concentration of odors of a single piece of almond chocolate, the plurality of odor detectors having different characteristics together comprising a single composite odor detector used in the odorimetric device of FIG. 1.

FIG. 4 is a graph plotting against time the output voltages of the five odor detectors, each being reprentative of the total concentration of odors of almond chocolate manufactured by "L" Corporation.

For these measurements, an odorimetric device which is identical to that shown in FIGS. 1A and 1B except using the composite odor detector was used. The ventilating fan 19 was turned on to introduce fresh ambient air into the odorimetric chamber 11 through the activated charcoal filter 18 to thereby deodorize the chamber. Then, a sample of chocolate was placed on the sample holder 28 and odorimetric chamber 11 was then sealed off. With the door 12 closed, the odor molecules emitted from the sample chocolate began to diffuse into the plenum of the chamber 11. The five odor detector showed changes in their electric resistances in response to exposure to the odor molecules, resulting in corresponding changes in the electric current flowing through the detectors. These current changes were transformed into corresponding changes in voltage, which were then amplified for subsequent recordal by a five-channel printer.

Five patterns of th curves, 1Ch to 5 CH, of the graph of FIG. 4 were compared with those which had beend erived from a sample chocolate of identical kind. This comparison revealed that the two sets of five curve patterns were in agreement with each other.

Thus, it will be appreciated that the present invention permits a quality inspection of food products such as chocolate by analytically comparing the total concentration of odors therefrom.

EXAMPLE 2

The total concentrations of odors from a relatively fresh orange and an orange left for one week were compared by the present odorimetric device.

Figure 5:
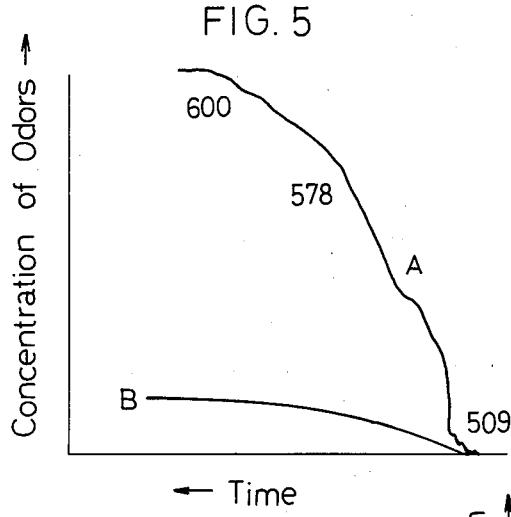
FIG. 5 is a plot against time of the total concentrations of odors of a relatively fresh orange and of an orange left for one week.

In FIG. 5, a curve a represents the total concentration of the odors of the relatively fresh orange, and a curve B shows the total concentration of the odors from the orange left for one week.

From FIG. 5, it can be recognized that the old orange B has a far lower odor concentration than the fresh one A. It can therefore be concluded that the total odor concentration of fruits such as oranges can be used in checking their freshness witht he odorimetric device according to the present invention.

EXAMPLE 3

Figure 6:
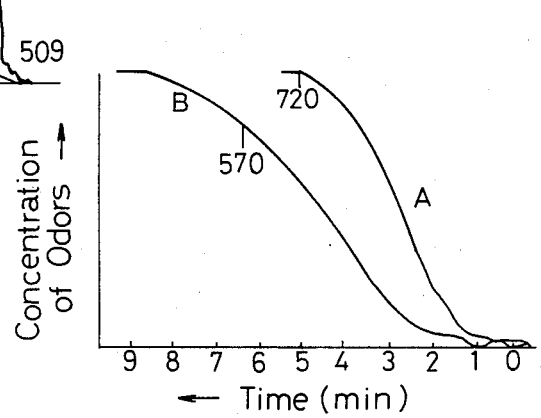
FIG. 6 is a plot against time of the total concentrations of odors of "Kilimanjaro" coffee just ground and of the same coffee left at a room temperature for one hour.

The present odorimetric device was used to compare the total concentrations of odors from "Kilimanjaro" coffee just ground and the one left at a room temperature for one hour. In FIG. 6, curve A indicates the value of the former coffee and curve B shows the latter. The results of such comparison indicate that coffee is very quick to lose its unique aroma. This will lead to the conclusion that aromatic foods and beverages and coffee as well will be subject to a quick dilution of unique aromas and therefore an early consumption thereof after exposure to the outside air is recommended.

EXAMPLE 4

Figure 7:
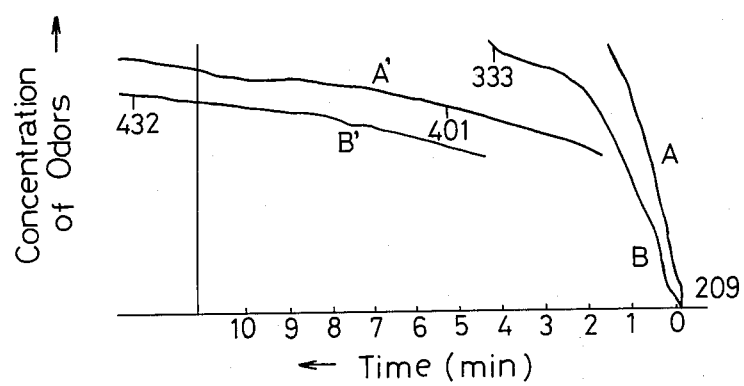
FIG. 7 is a plot against time of the total concentrations of odors of Japanese traditional spirits called the "Shochu" just distilled and the same "Shochu" matured for twenty years.

The present odorimetric device was used to compare Japanese traditional spirits called "Shochu" just distrilled and the one which were matured for twenty years. In FIG. 7, curves A and A' correspond to the younger "Shochu", and curves B and B' correspond to the matured "Shochu". The gain of the DC amplifier was switched to change the scale from curves A and B to curves A' and B' to thereby enable tracking of the changing total concentration of odors. Comparison of the curves indicates that the total concentration of aromas or odors of "Shochu" is the highest when just distilled.

If a sample is thus specified, the progress of the maturing process can be monitored by measuring the total concentration of odors of the spirits, which will permit and easy evaluation of the aging thereof.

EXAMPLE 5

Figure 8:
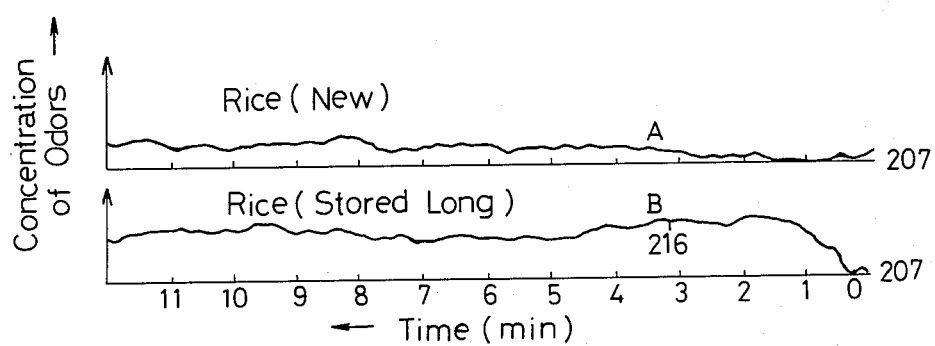
FIG. 8 is a plot against time of the total concentrations of odors of fresh rice and of stale rice.

Another comparison was made between fresh rice and stale rice using the present odorimetric device. In FIG. 8, a curve A corresponds to the fresh rice, and a curve B corresponds to the stale rice (i.e., the crop of 1981). From FIG, 8, it can be concluded that the stale rice has a stronger smell. This will indicate that the quality of the starch and protein contained in rice could be evaluated from the measurement of its delicate odors.

EXAMPLE 6

Figure 9:
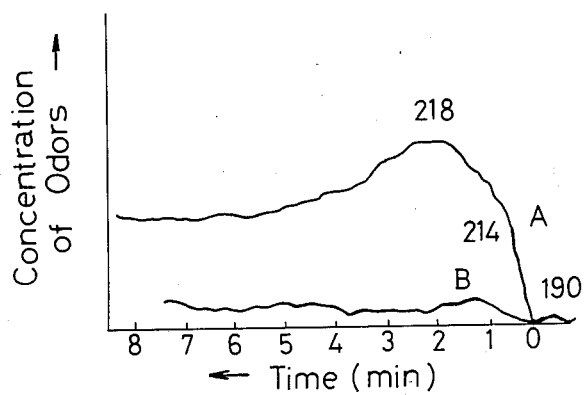
FIG. 9 is a plot against time of the total concentrations of odors of a stock solution for commercially available soy sauce and of the same soy sauce prepared by diluting the stock solution with five times as much city water as the solution.

Using the present odorimetric device, a stock solution for commercially available soy sauce was compared with soy sauce which was prepared by diluting the stock solution with five times as much city water as the solution. In FIG. 9, a curve A plots the total concentration of odors of the stock, and a curve B shows that of the diluted soy sauce. The graph reveals that the odors of the stock solution are considerably lost if it is diluted five times. This example may well be utilized as a convenient technique for evaluating the deodorizing effect in a food manufacturing process.

As has been described above, the present invention enables a real time measurement of the concentration of odors of an object without making a direct contact therewith. This makes it possible to quantitatively evaluate the freshness of certain foods such as fruits and rice and also the degree of maturity of certain alcoholic beverages in a more efficient and reliable way than conventional organoleptic tests.

The present invention also permits an instantaneous evaluation of whether an object to be measured has an acceptable quality by measuring the total concentration of odors of the object, followed by comparing the measured concentration value with a reference value previously derived from typical objects of the same kind. Accordingly, it is possible to perform quality inspections in a quick and efficient manner with the prevent odorimetric device.

Furthermore, the present odorimetric device is relatively simple in construction and inexpensive to manufacture, which lends itself to a real time evaluation of the freshness of perishable goods. Moreover, the present invention can find widespread use in the food production industry, especially where there is the need for a quick and reliable quality inspection at the time of food production and shipment.

We claim:

1. A method of measuring the total concentration of odors of an object using an odorimetric device including a non-selective odor detector disposed within an odorimetric chamber, comprising the steps of:
   (a) heating a non-selective odor detector to a predetermined temperature at which the rate of adsorption and desorption of odors of an object to be measured is sufficiently high to enable a real time measurement of the total concentration of the odors;

(b) introducing fresh air into an odorimetric chamber defined in the odorimetric device to scavenge the odorimetric chamber;

(c) placing the object in the odorimetric chamber;

(d) sealing off the odorimetric chamber from the surrounding environment; and (e) monitoring the total concentration of the odors of the object.

2. A method according to claim 1, wherein the monitoring step (e) is carried out after the output reading of the odor detector has become stable.

3. A method according to claim 1 or 2, further comprising:

(f) comparing the monitored total concentration of the odors of the object with a reference value indicative of that of a typical object of the same kind as the object to be measured.

4. A method according to claim 3, wherein the reference value is obtained as the total concentration of odors of a representative sample by subjecting the sample to the steps (a) to (e).

5. A method according to claim 1, further comprising:

(g) recording the monitored total concentration of odors as a function of time.

6. A method according to claim 5, further comprising: (h) comparing the recorded total concentration of the odors with a reference pattern indicative of a typical change of the total concentration of odors of a reference sample.

7. A method according to claim 1, wherein the non-selective odor detector includes: a sensor portion made of a simple substance of an n-type semiconductor having its electric resistance variable in response to adsorption and desorption of gas molecules; and a heater for maintaining the sensor portion at a pre-determined temperature.

8. A method according to claim 7, wherein the n-type semiconductor is a highly purified metal oxide selected from the group comprising tin oxide and zinc oxide.

9. A method according to claim 8, wherein the metallic oxide is formed into a sintered body or film.

10. A method according to claim 1, wherein the non-selective odor detector comprise a plurality of like odor detector elements, each including a sensor portion and a heater for maintaining the sensor portion at a predetermined temperature, the plurality of like odor detector elements being arranged to have different sensing characteristics by applying voltages of different magnitudes to their respective heaters.

11. A method according to claim 10, wherein the non-selective odor detector has a plurality of outputs developed by the plurality of odor detector elements as indicative of the total concentrations of odors of an object to be measured, the plurality of outputs being adapted for comparison with a like plurality of reference outputs which have been derived from a measurement of a reference sample, to see if the respective pairs of outputs are matched for the purpose of discriminating the object in relation to the reference sample.

12. An odoriometric device for measuring the total concentration ofodors of an object, comprising:

(a) a housing defining therein an odorimetric chamber for accommodating an object to be measured;

(b) a door for sealingly closing the odorimetric chamber from the surrounding environment;

(c) a non-selective odor detector mounted within the odorimetric chamber for monitoring the total concentration of odors emitting from the object;

(d) heater means for heating the non-selective odor detector to a predetermined temperature at which the rate of adsorption and desorption of odors of the object to be measured is sufficiently high to enable a real time measurement of the total concentration of the odors;

(e) means for introducing fresh air into the odorimetric chamber to scavenge it;

(f) display means for providing an instantaneous indication of the monitored total concentration of the odors.

13. An odorimetric device according to claim 12, wherein the means for introducing fresh air includes a bed of surface active sorbent such asactivated charcoal through which the introduced air is filtered into clean air.

14. An odoriometric device according to claim 13, wherein the means for introducing fresh air includes a ventilating fan for introducing the cleaned ambient air passing throug the bed of surface active sorbent into the odorimetric chamber to thereby make it free of odors.

15. An odorimetric device according to claim 12, further comprising a shutter mechanism operative to isolate the nonselective odor detector from the odorimetric chamber when not in use.

16. An odorimetric device according to claim 12, further comprising a recorder for recording the monitored total concentration of odors as a function of time.

17. An apparatus according to claim 12, wherein the non-selective odor detector includes: a sensor portion made of a simple substance of an n-type semiconductor having its electric resistance variable in response to adsorption and desorption of gas molecules.

18. An odorimetric device according to claim 17, wherein the n-type semiconductor is a highly purified metal oxide selected from the group comprising tin oxide and zinc oxide.

19. An odorimetric device according to claim 17, wherein the sensor portion comprises a film of metal oxide deposited on a substrate, the odor detector including a pair of electrodes sandwiching both ends of the sensor portion; a pair of insulators for fixedly mounting the sandwiched sensor portion thereon.

20. An odorimetric device according to claim 18, wherein the sensor film is made of tin oxide having a purity of 99.999%, wherein the substrate is made of a ceramic plate having a thickness of 0.6 mm, and wherein a binder of aluminum oxide is used.

21. An odorimetric device according to claim 12, wherein the heater means has a resistance of about 10 K$\Omega$ and is supplied with a voltage of 2 to 6 V.

22. An odorimetric device according to claim 12, wherein the non-selective odor detector comprises a plurality of like odor detector elements, each including a sensor portion, the heater means comprising a plurality of like heater elements each associated with one of the odor detector elements, the plurality of like odor detector elements being arranged to have different sensing characteristics by applying voltages of different magnitudes to their associated heaters.

23. An odorimetric device according to claim 22, wherein the non-selective detector has a plurality of outputs developed by the plurality of odor detector elements as indicative of the total concentrations of odors of an object to be measured, the plurality of outputs being adapted for comparison with a like plurality of reference outputs which have been derived from a measurement of a reference sample, to see if the respective pairs of outputs are matched for the purpose of discriminating the object in relation to the reference sample.

* * * * *